United States Patent [19]
Smith et al.

[11] Patent Number: 5,505,313
[45] Date of Patent: Apr. 9, 1996

[54] METHOD AND APPARATUS FOR DETECTING DIAMONDS IN A PLURALITY OF OBJECTS

[75] Inventors: Martin P. Smith, Wargrave; Robin W. Smith, Croydon, both of England

[73] Assignee: Gersan Establishment, Vaduz, Liechtenstein

[21] Appl. No.: 107,813

[22] PCT Filed: Feb. 20, 1992

[86] PCT No.: PCT/GB92/00295

§ 371 Date: Nov. 5, 1993

§ 102(e) Date: Nov. 5, 1993

[87] PCT Pub. No.: WO92/14556

PCT Pub. Date: Sep. 3, 1992

[30] Foreign Application Priority Data

Feb. 20, 1991 [GB] United Kingdom ............... 9103552

[51] Int. Cl.$^6$ ................................................ B07C 5/00
[52] U.S. Cl. ....................... 209/579; 209/587; 209/589; 356/30
[58] Field of Search ............................... 209/577, 579, 209/587, 589; 356/30, 301; 250/458.1, 461.1

[56] References Cited

U.S. PATENT DOCUMENTS

| | | | |
|---|---|---|---|
| 4,799,786 | 1/1989 | Gerrard | 356/30 |
| 4,875,771 | 10/1989 | Bowlely et al. | 356/30 |
| 4,900,147 | 2/1990 | Bowley et al. | 356/30 |
| 4,919,533 | 4/1990 | Bowley et al. | 356/30 |
| 5,118,181 | 6/1992 | Yifrach et al. | 356/30 |
| 5,143,224 | 9/1992 | Burchell | 209/579 |
| 5,206,699 | 4/1993 | Stewart et al. | 356/30 |
| 5,351,117 | 9/1994 | Stewart et al. | 356/30 |

FOREIGN PATENT DOCUMENTS

| | | |
|---|---|---|
| 0064842 | 11/1982 | European Pat. Off. |
| 0345949 | 12/1989 | European Pat. Off. |
| 2121535 | 12/1983 | United Kingdom. |
| 2140555 | 11/1984 | United Kingdom. |
| 2165943 | 4/1986 | United Kingdom. |
| 2198551 | 6/1988 | United Kingdom. |
| 2199657 | 7/1988 | United Kingdom. |
| 2219080 | 11/1989 | United Kingdom. |
| 2219394 | 12/1989 | United Kingdom. |
| 2228317 | 8/1990 | United Kingdom. |
| WO86/07457 | 12/1976 | WIPO. |
| WO87/03963 | 7/1987 | WIPO. |
| WO88/01378 | 2/1988 | WIPO. |
| WO88/05534 | 7/1988 | WIPO. |
| WO88/07189 | 9/1988 | WIPO. |
| WO88/07213 | 9/1988 | WIPO. |

*Primary Examiner*—D. Glenn Dayoan
*Attorney, Agent, or Firm*—Rosen, Dainow & Jacobs

[57] ABSTRACT

In order to sort ore from associated mineral material, a method and apparatus of classifying an object is provided, the method including feeding the object along a feed path, irradiating the object with infra-red radiation of a first wavelength, the radiation of the first wavelength being focussed onto an irradiation zone intersecting the feed path, the irradiation zone having a length in the vertical plane substantially greater than its width in the vertical plane. The intensity of radiation emitted by the object at at least one second wavelength different from the first wavelength is examined, the second wavelength being characteristic of a first class of object or the ore to be sorted from the mineral, whereby the classification of the object may be derived.

13 Claims, 7 Drawing Sheets

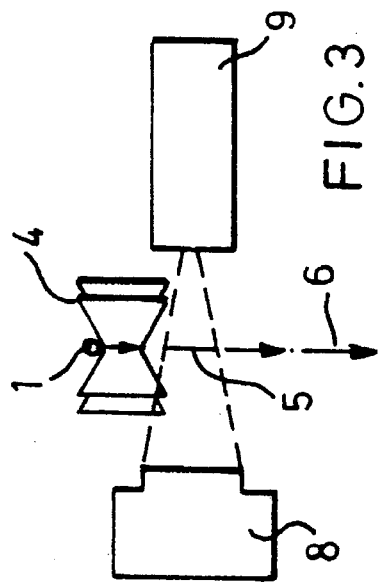
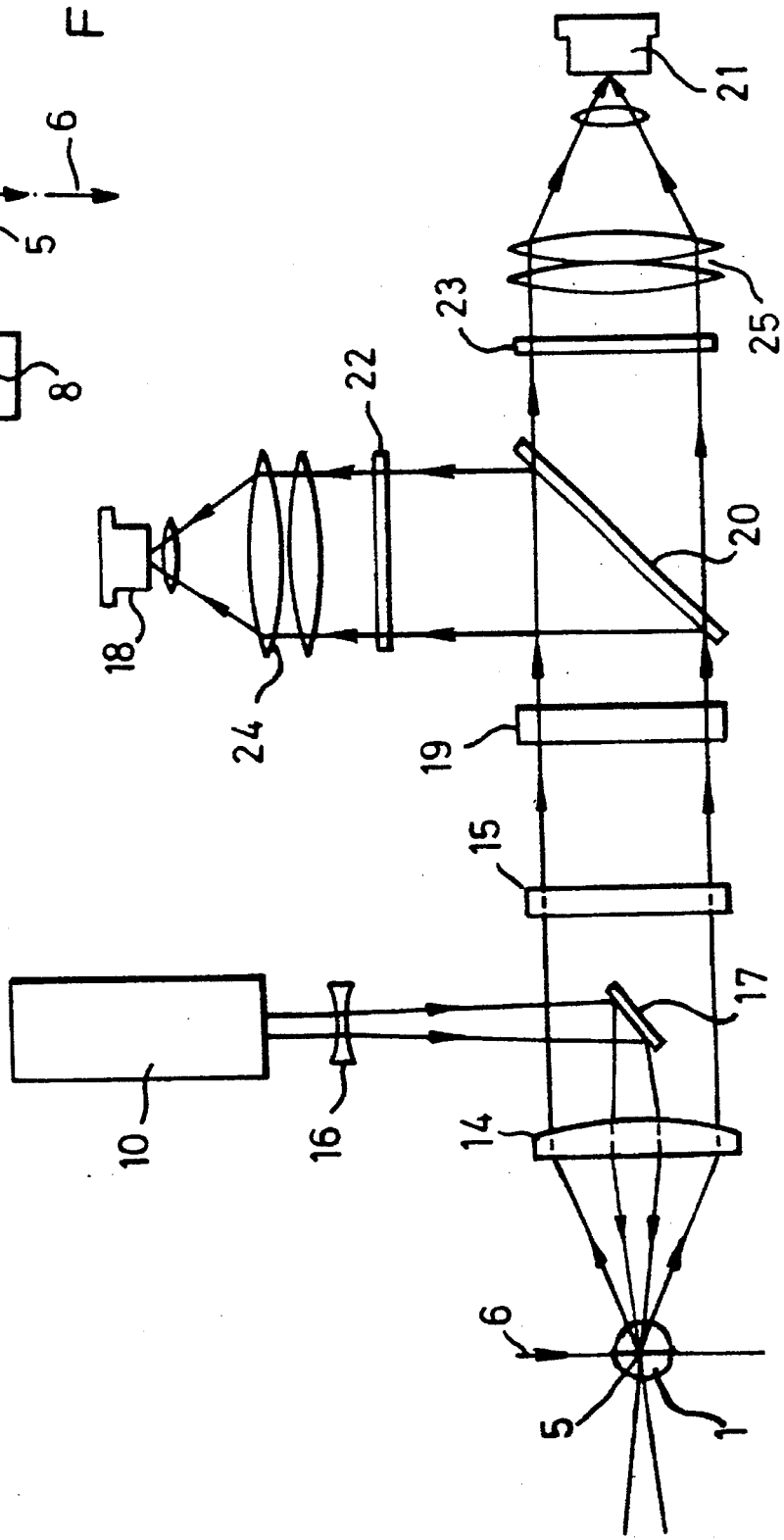

METHOD AND APPARATUS FOR DETECTING DIAMONDS IN A PLURALITY OF OBJECTS

BACKGROUND OF THE INVENTION

This invention relates to classifying or sorting objects, for instance for sorting ore from associated mineral material or sorting diamonds from gangue in the diamond mining industry.

Diamonds can be mined from deposits in rock and in this process it is necessary to crush the rock and then sort the diamonds from the gangue or unwanted material. A process for achieving a primary sort of gangue from diamonds is disclosed in European Patent Application No. EP-A-0 345 949 filed by the Applicants. In this process mixed diamonds and gangue are fed on a broad belt feeder, a narrow transverse strip of which is irradiated by X-rays or visible radiation, the fluorescence or Raman emission of diamond being detected to give a signal and locate the diamond. This signal actuates means for selecting diamonds from the stream of mixed material and directing them to a bin to give a diamond rich concentrate. However, other non-diamond mineral particles also fluoresce under the X-ray irradiation or exhibit broad band luminescence stimulated by the excitation source, e.g. a laser operating in the UV/visible portion of the spectrum. This laser excited broad band luminescence covers the region that is specifically examined for detecting the characteristic Raman shift for diamond. This broad band laser induced luminescence is falsely identified as a Raman shifted response and thus other mineral particles can be falsely identified and selected as diamond. Additionally, as this primary sorter is a high-mass sorter, the diamond and gangue mixture is fed on a wide belt and the diamond selecting means may select the particles sitting next to the fluorescing particle on the belt as well. Thus the machine can only produce a diamond/luminescing mineral/gangue concentrate. Traditionally this concentrate is hand sorted which is laborious, and as some of the minerals are fairly similar in appearance to the diamonds, can be difficult and unreliable.

In addition to the primary sort achieved by this type of machine, it is necessary to provide a machine for achieving a more accurate sort on the concentrate produced by the process, and remove the other non-diamond material collected in the primary process.

Methods of classifying diamonds by studying them with radiation are generally known (for example EP-A-0345949 as above) but it is desirable to provide a method of classifying diamonds and other objects using radiation in which the problem of the varying trajectories obtained with objects of different sizes and shapes without expensive object projecting means is avoided.

THE INVENTION

A first aspect of the invention provides a method and apparatus for classifying an object.

The objects may be irradiated in a zone which is of sufficient extent to intersect the trajectories of all objects, which may have different trajectories due to differing size and shape, the irradiation zone being such that the local radiation intensity is enough to cause substantial excitation of objects of interest. However, the irradiation zone should be as small as is practical, so that the power input required to achieve the necessary radiation intensity is not too high. This sufficient intensity of radiation may be achieved by focussing a beam of irradiating radiation onto a relatively small area, for example a line focus. Where a focus is used, the irradiation zone will correspond to the region at the focus. Where the irradiation zone is much longer than it is wide, it is substantially linear. The irradiation zone is preferably defined by a section of a straight line, but it could be slightly curved. The exact shape of the irradiation zone in said substantially vertical plane need not be of any specific shape-it could be ellipsoid, retangular, triangular etc.

In the present application, a beam of light is considered to be focussed if it is brought to a focus in a first plane, even if it is not brought to a focus in a second plane at right angles to the first plane.

Often, objects fall at different rates due to differing size and shape. They will accelerate in the vertical direction at different rates, thus changing their vertical component of velocity differently. Although they are projected with the same initial velocity, their trajectories will differ. As the irradiation zone lies in the plane in which the various possible trajectories will lie, the object must pass through the irradiation zone. However, more generally, this aspect of the invention has applicability where the object can follow one of a number of paths in the same plane, the irradiation zone lying in the plane. The first aspect of the invention is therefore of use where the trajectory of objects is not known exactly, in particular, where the objects have travelled sufficiently far from a projecting means to have an unknown vertical component of velocity. This allows a simple projecting means to be used, with no complex apparatus for controlling the trajectories of the objects.

In addition to providing an irradiation zone that will catch the trajectories of all objects, the first aspect of the invention also provides a detection zone which lies substantially in the substantially vertical plane, and intersects the trajectory. The detection zone may comprise a zone of a length in said vertical plane substantially greater than its width in said vertical plane. For example, the ratio of said length to said width could be greater than 3 to 1 and is preferably around 10 to 1. The detection zone may be substantially linear and may be substantially coincident with the irradiation zone, or slightly larger than it. The detection zone may extend at a large angle to the trajectory. This form of the detection zone allows emissions from objects at different positions in the irradiation zone to be collected and identified. At the same time, the detector need not be very large because the detected area is relatively small. When the first aspect of the invention is used with a Raman spectroscopic technique, the radiation zone and detection zone are substantially coincident as the emission of the Raman scattered radiation is near instantaneous. Where slower processes, such as luminescence are used, the detection zone may be displaced with respect to the irradiation zone, being located further down the trajectory.

The second aspect or third aspect of the invention may be used with the method or apparatus of the first aspect of the invention, with the objects being in a free trajectory when they are irradiated. However, the objects could be fed through the irradiation zone on a belt, with an irradiation zone comprising a spot, or a line, or a plane extending across the belt. The embodiment having objects in a free trajectory is useful for providing a more accurate sort of the diamond/gangue concentrate produced by the process of European patent application no. EP-A-0345949.

The embodiment of the third aspect of the invention employing a belt may be used at an earlier stage of processing, between the primary and secondary crushers of the extraction process. Lumps of ore, for instance 30–100 mm diameter leave the primary crusher and may contain very large diamonds. The apparatus of the third aspect of the invention could be used to inspect objects arriving one-at-a-time on a belt, to detect diamonds. If a large or high quality diamond were detected (giving a large Raman signal level) the belt would be stopped automatically to prevent the diamond reaching the secondary crusher. The apparatus of the third aspect of the invention may be preferred to that of European patent application no. EP-A-0345949, as it is cheaper and as the number of objects to be studied (the partly crushed ore) is fewer.

The invention will now be further described by way of example and with reference to the accompanying drawings, in which:

BRIEF DESCRIPTION OF THE DRAWINGS

FIG. 3 is a view along Section III—III of FIGS. 1 and 2;

FIG. 4 is a schematic plan view of the optical system of the machine of FIG. 1;

DETAILED DESCRIPTION OF THE DRAWINGS

Figure 1:
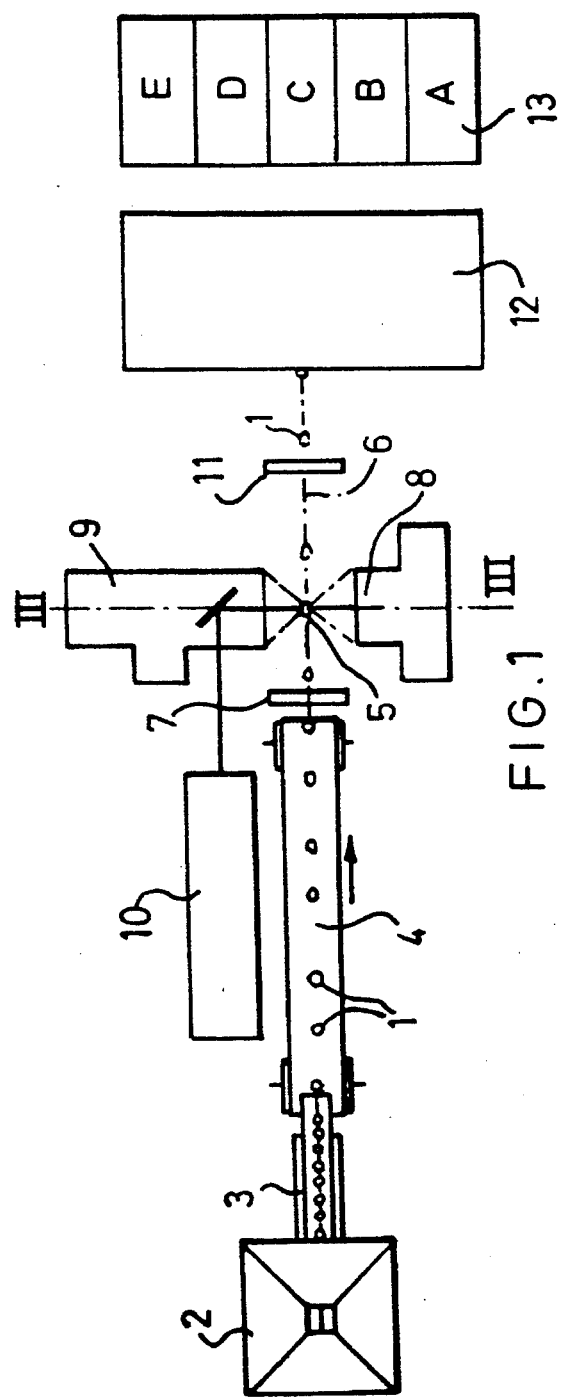
FIG. 1 is a schematic plan view of a first embodiment machine for classifying objects according to the invention.
Figure 2:
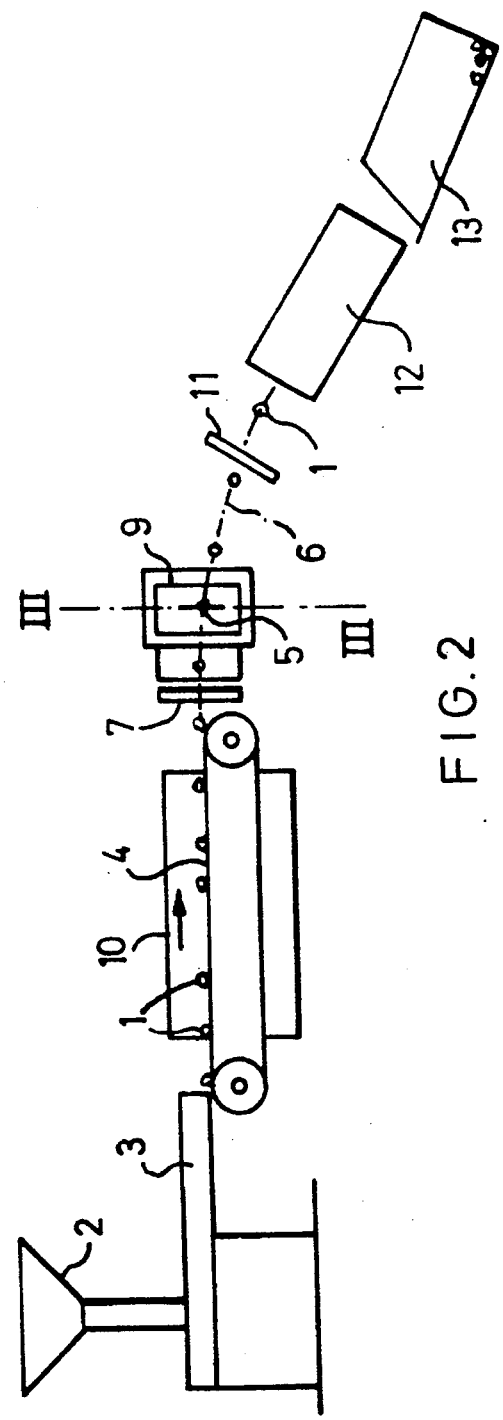
FIG. 2 is a schematic elevation of the machine of FIG. 1.

FIGS. 1 and 2 show a machine or apparatus in which objects or particles 1 are fed singly through a detection zone and analysed by the optical system shown. The machine is intended to be used to sort diamonds from gangue in a diamond/gangue mixture which has already been subject to a first order sort, for instance by the low broad band luminescence technique as described in EP-A-0 345 949. In particular, the machine may use the spectroscopic technique described in relation to FIGS. 8a, 8b, 8c and 8d hereof, in which the object is irradiated with infrared radiation and its Raman emission is studied. The mixture obtained with this technique represents a very much smaller quantity of material, and a simple and relatively slow feed is sufficient for the satisfactory operation of the apparatus of the present invention.

FIGS. 1 and 2 show the arrangement of the belt 2 and the collection bins for collecting diamonds of a different quality, as shall be explained hereinafter.

The objects 1 are fed into a hopper 22 of the machine to feed a stream of objects 1 onto a vibratory feeder 3 which delivers the objects 1 substantially one at a time onto a feed belt 4, which is preferably a V-belt. In the preferred embodiment, there is no provision for detecting spatial location in the detection zone 5. Accordingly, objects must be fed individually through the detection zone 5. The hopper 2, feeder 3 and belt 4 are shown schematically as suitable feed systems are known and available.

Objects 1 are projected from the belt 4 with a substantial forward linear velocity so that they follow the trajectory 6 into the detection zone 5. Before reaching the detection zone 5, the objects or particles 1 pass through a light curtain 7 providing a signal which triggers a detector to record and process the emissions of the objects 1. Optionally, size detection means may be provided in the form of a sensor 8 which senses the objects 1 as a shadow against laser irradiating radiation projected by system 9 from laser 10; the sensor 8 can be associated with a heat sink as shown in FIG. 1. A further light curtain 11 is provided to signal the arrival of the objects 1 at the sorting station or dispenser 12 where the objects are directed, according to their classification, into bins A, B, C, D or E at 13. As set out below, system 9 also comprises the detector.

Objects 1 are projected from the end of the belt 4 with a fixed initial forward linear velocity so that they fall under gravity through the irradiation zone 5 along a trajectory 6 which lies in a substantially vertical plane (as shown in FIG. 3) but which is not itself substantially vertical (as shown in FIG. 2). In the irradiation zone 5, the objects are irradiated or illuminated with radiation from laser 10.

Figure 5:
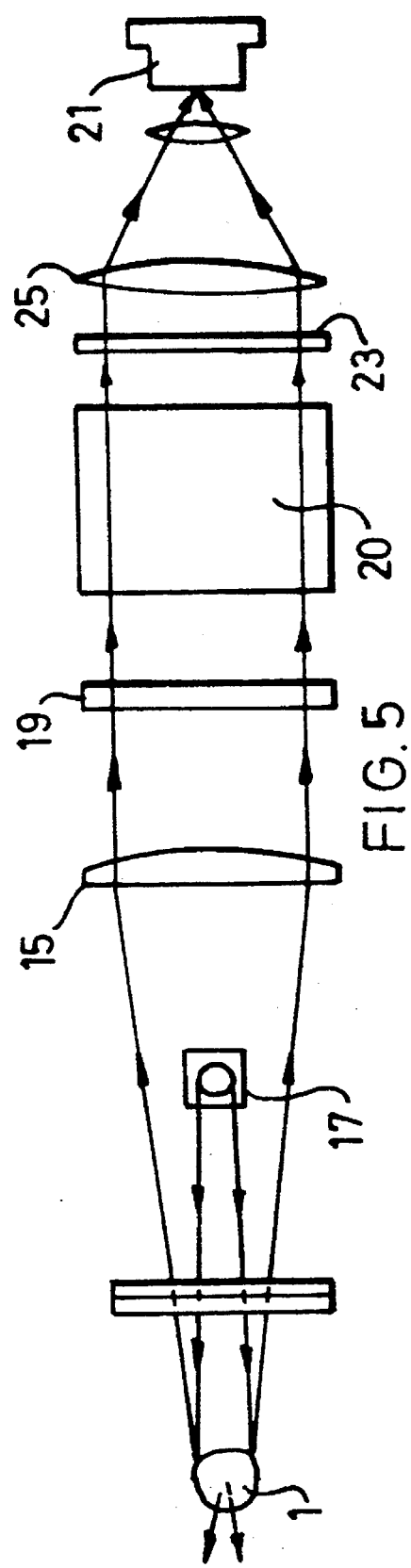
FIG. 5 is a schematic elevation of the optical system of FIG. 4.

FIGS. 4 and 5

Both the laser irradiating system 9 and the scattered light imaging system are focussed onto a single line focus 5 which is orientated at a large angle or generally at right angles to the trajectory 6 and which lies in the vertical plane containing the trajectory 6. In practice, the line focus can be strictly vertical, i.e. at about 80° to the trajectory 6, an angle of say about 60° to 90° to the trajectory 6 being satisfactory. This is achieved by a cylindrical lens 14 as shall be described in detail hereinafter. The laser beam produced by the laser 10 is first spread out by a diverging lens 16 and is then directed towards the object by a mirror 17 before being focussed onto a line by the cylindrical lens 14.

The cylindrical lens 14 also collects light emitted by the object 1 and with cylindrical lens 15, produces a substantially collimated rectangular beam of such light. Before collected light is directed to the detector 18, radiation of the irradiating wavelength is removed by filter 19. The light is then passed through a beam splitter 20 which produces two independent beams which are directed at separate detector means 21 and 18.

This allows two separate wavelengths emitted by the object to be studied independently. Narrow band pass filters 22 and 23 of suitable band pass may be provided, and focussing systems 24 and 25 are used to direct the radiation onto detectors 18 and 21 respectively.

FIG. 6

Figure 6:
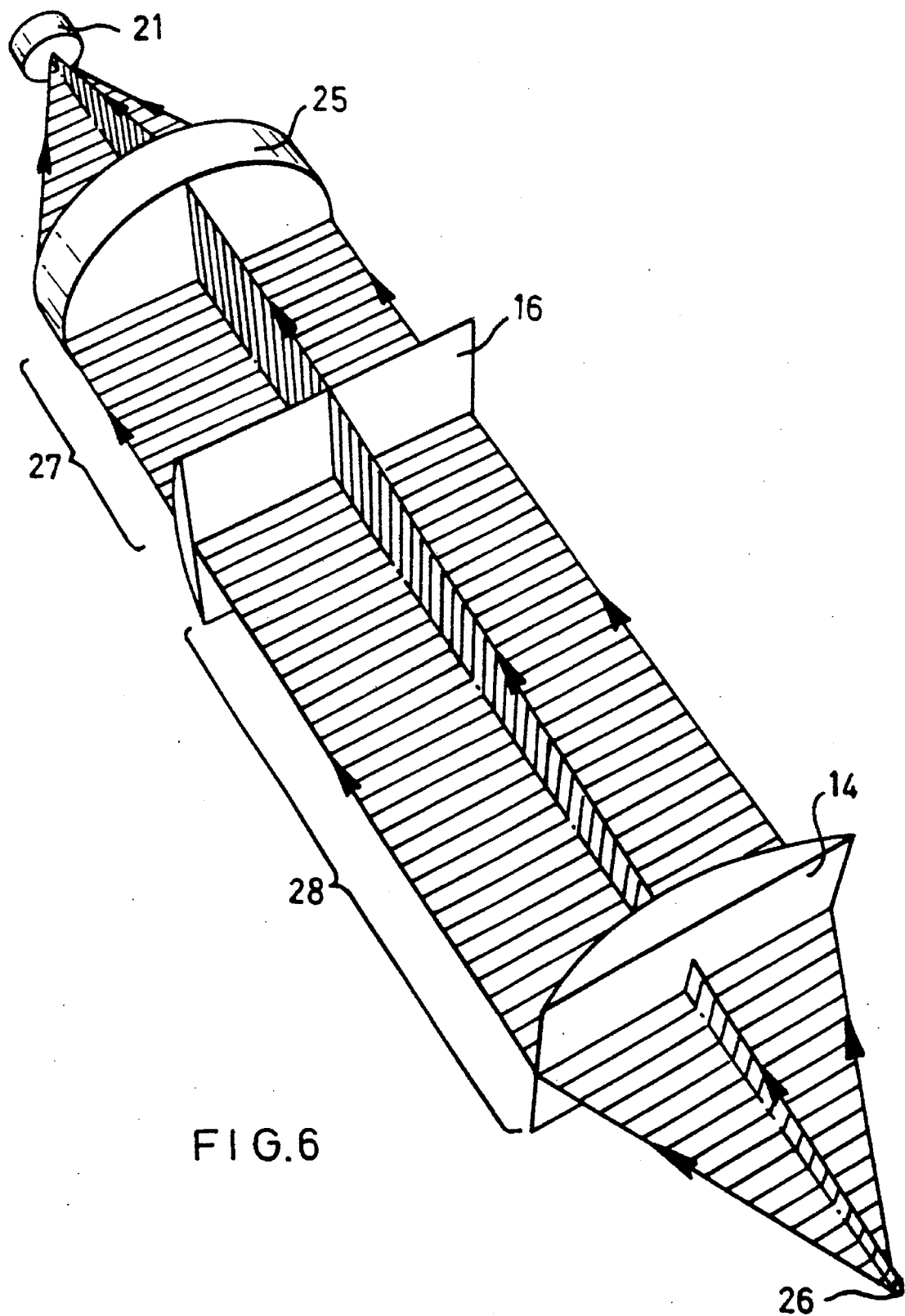
FIG. 6 is a ray diagram of part of the optical system of the machine.

FIG. 6 is a ray diagram for the cylindrical lenses 14 and 15; only the optics for the detection means 21 is shown, the optics for the further detection means 18 and the irradiating laser 10 being omitted for clarity. The machine is preferably set up to observe the line focus 5 referred to above, which will extend roughly normal to the plane of the drawing. An aperture or detection zone 26 extending for example 9 mm in the direction at right angles to the trajectory 6 and 1 mm in a direction parallel to trajectory 6 is observed.

As can be seen from FIG. 6, the cylindrical lenses 14 and 15 comprise convex lenses which are chords of cylinders (as opposed to chords of spheres, as is normally the case with lenses), and which are set up to independently focus radiation along two axes at right angles. As a result of passing through the cylindrical lenses 14 and 15, a substantially parallel beam of radiation as emitted by the object 1 is produced in the region 27. It is in this region 27 that the beam splitter 20 may be located. A further lens system 25 which shall not be described here is provided to produce for example a 1 mm by 3 mm focus on the detection plane of the detector 21. The mirror 17 for directing the irradiating radiation from the laser 10 onto the detection zone 26 is located in the region 28 at such a position that it is focussed by the cylindrical lens 14 of the imaging system so that the line focus of the optical system coincides with the line focus of the irradiation system. This ensures that the imaging and projection systems are always confocal and any object passing through the irradiation zone is automatically in the detection zone.

The detection zone 26 is generally coincident with the line focus 5 referred to above, ie is in a vertical plane containing the trajectory 6 and is generally at right angles to trajectory 6. In general, the trajectories 6 of all objects 1 of different sizes will lie in the same vertical plane. However, as the objects 1 are of varying size and shape, they will fall at different rates *due to their different sizes although they all have the same initial linear velocity due to the belt 4. The detection zone 26 lies in this vertical plane (the vertical plane passes substantially through the line of projection of the belt 4). A sharp focus can be obtained, but it is still possible to irradiate and observe objects having different trajectories. In general the line focus or irradiation zone 5 will be longer and thinner than the detection zone 26. The line focus is capable of producing a signal dependant upon the size of the objects if objects of a substantial range of sizes are to be observed.

Figure 7:
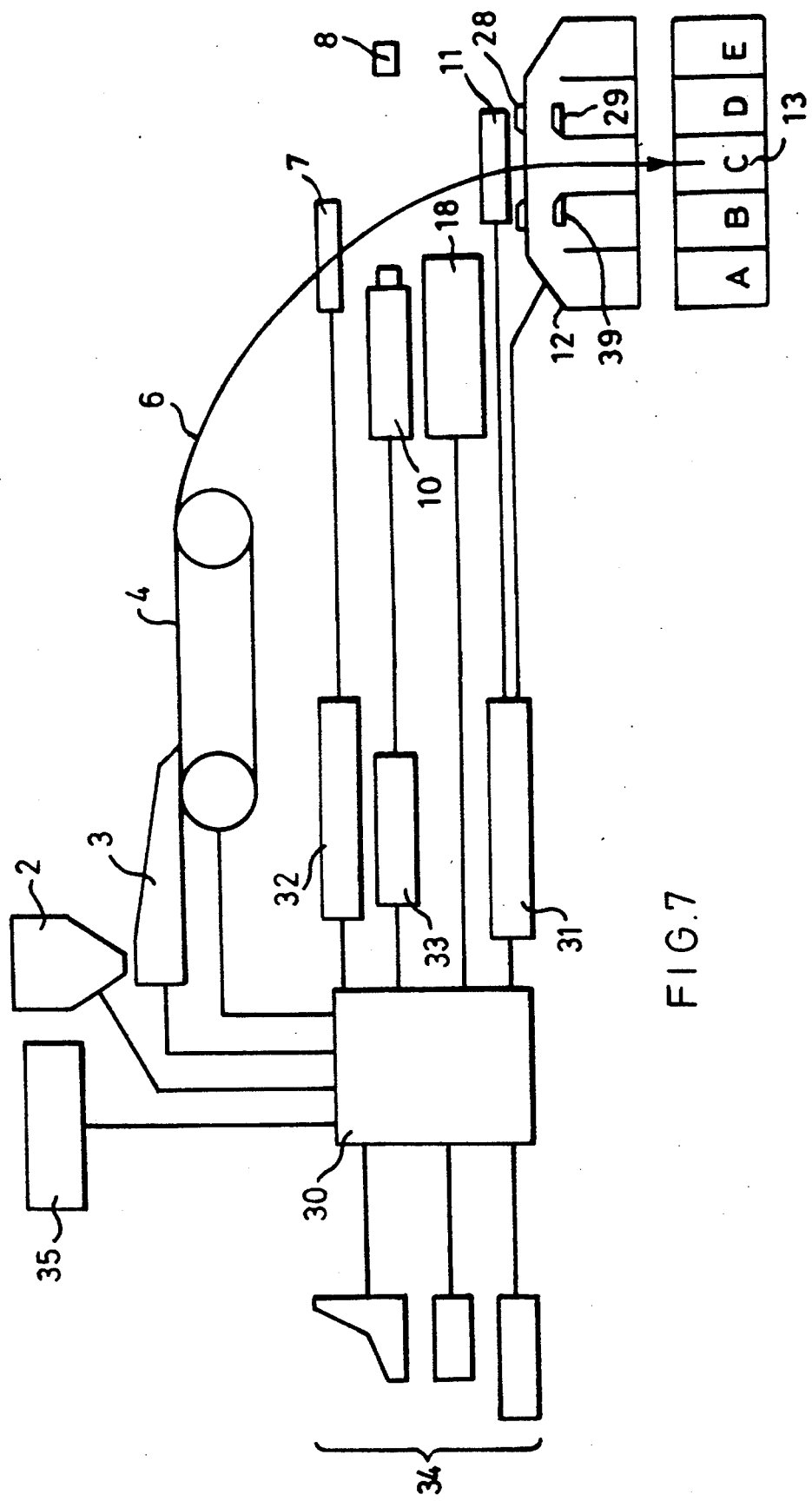
FIG. 7 is a schematic drawing of the control systems for the machine.

FIG. 7 is a schematic illustration of the control systems for a machine according to FIGS. 1 to 6. The machine of FIG. 7 may be used to sort diamonds from Gangue using the method described in relation to FIGS. 8a to 8d or to sort diamonds according to quality, as described herein below FIG. 7 includes schematic representations of the hopper 2, vibratory feeder 3, feed belt 4, trajectory 6, light curtains 7 and 11, detector 8, laser 10 and dispenser 12. The dispenser 12 comprises a set of air jets 28 and 29 controlled by a processing means or main control processor 30-such sorting stations are known and available. Processor 32 receives a signal from light curtain 7 when the object enters the viewing zone and give a signal to main processor 30 to begin processing of incoming data. The main processor 30 receives signals from the detector 18 and, optionally, the sensor 8. Preferably, the sensor 8 senses presented area or specifically the attenuation of the laser signal as the object 1 passes through the line focus, but as an alternative the sensor 8 could merely signal the length of time the stone takes to pass through the line focus; the former is preferred as it is more responsive to shape. A decision is then made as to whether the object 1 is a diamond or not. Furthermore, as shall be described hereinafter, the signals may be used to make a first order sort of quality of diamond. Signals dependent on whether the object 1 is a diamond or not, or dependent on the quality of the diamond are fed to a sort processor or air jet controller 31 which activates an air jet 28 and/or 29 to direct the object 1 into one of a number of appropriate diamond/gangue or diamond quality bins 13 labelled A to E.

Alternatively, the bins 13 may be graded according to the confidence of the sort. The signal from the detection means is normalized according to the size of the object, 1 so that any object 1 giving a strong signal has a high probability of being diamond and will be directed into the high confidence sort bin. Objects 1 giving a lower signal are less certainly diamond and will be directed to a lower confidence sort bin, whilst those giving zero or negative signals are almost certainly gangue.

The laser 10 is controlled by the main processor 30 via an interlock system 33. The main processor 30 can be monitored and operated by a systems operator using the visual display unit, key pad and control panel indicated generally at 34.

As stated above, the machine can be used for a primary quality sort. The size of the Raman signal generated depends upon the volume of diamond crystal excited, and upon its quality. Better quality gem stones (with fewer cracks and internal absorbing features) give higher signals. In general, the particles will be pre-screened into size fractions before being fed into the machine, so that the size factor is effectively taken care of. The sensor 8 may be us ed to give signals to the main processor 30 representative of the size of the object 1. A compensation factor dependent upon the size of the object 1 may then be used in the decision algorithm used by the main processor 30. Given that the size of the object 1 is known or measured, objects 1 showing high emissions at the Raman scattering wavelengths may be assumed to be of a generally high quality. Lower signals will represent poor quality diamonds, and substantially zero signals will represent gangue. On the basis of this information, the air jet controller 31 may be used to control the series of air jets 28, 29 so that the objects 1 can be delivered into one of a series of graded classes A-E from gangue to high quality diamond. Furthermore, as diamonds are a very high value product, the machine can be operated at high levels of security and high quality diamonds identified by the process may be delivered to an even higher security level within the high security system. A security system 35 can interface the main control processor to detect and isolate high quality diamonds and prevent unauthorised access.

FIGS. 8a, 8b, 8c and 8d

Figure 8A:
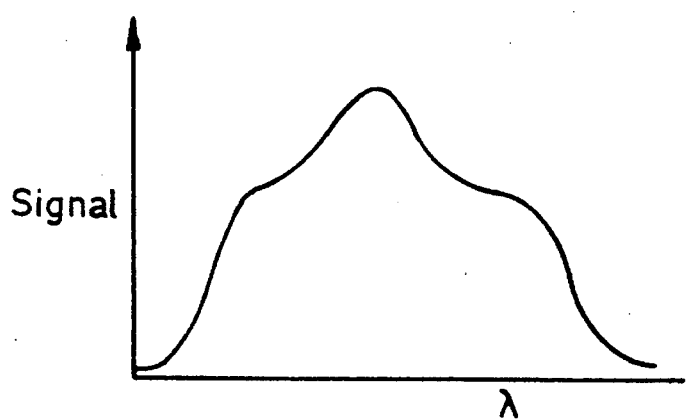
FIGS. 8a, 8b, 8c and 8d show schematic graphs of the photoluminescence characteristics of diamond and associated mineral, compared to the band pass characteristics of filters used in the machine of FIG. 1.
Figure 8B:
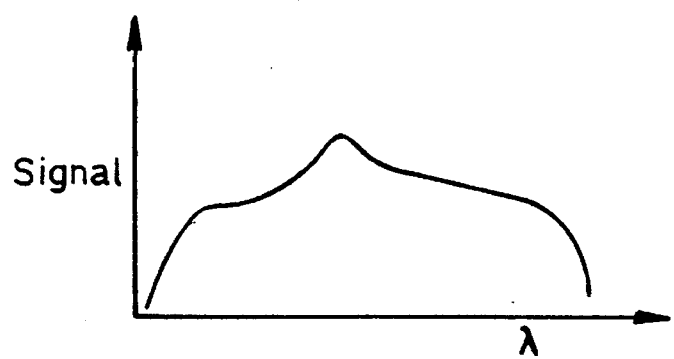

FIGS. 8a and 8b show the X-ray photoluminescence signal due to diamond (FIG. 8a) and due to mineral showing diamond like fluorescence (FIG. 8b). X-ray fluorescence is not sufficient to distinguish diamonds from certain types of minerals.

The apparatus of any of FIGS. 1 to 7 may be used with infrared illuminating radiation to distinguish diamonds from other host minerals with which diamond may be associated when mined.

Figure 8C:
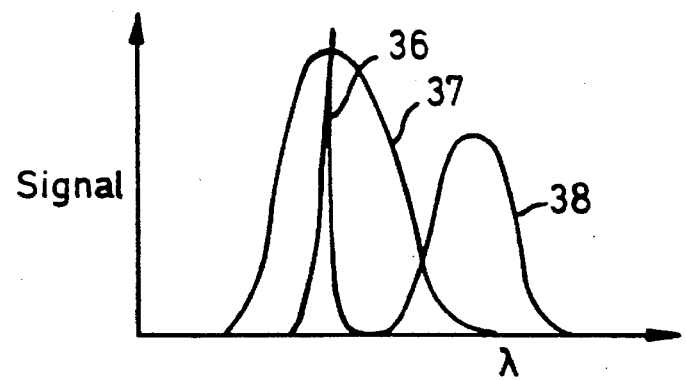

FIG. 8c shows the infra-red Raman peak 36 for diamond, superimposed upon the band-pass characteristics 37 of the filter 23 and the band-pass characteristics 38 of the filter 22. Similarly, FIG. 8d shows a typical infra-red luminescence signal 39 due to mineral superimposed upon the characteristics 37 and 38 of filters 23 and 22 respectively.

The signals detected by the detectors 18 and 21 depend upon the width of the infra-red Raman peaks and their overlap with the filter characteristics. In the case of FIG. 8c, a high infra-red Raman diamond signal will be produced, and the infra-red Raman side band signal will be almost zero. When the latter is subtracted from the former, a high positive value is produced.

Figure 8D:
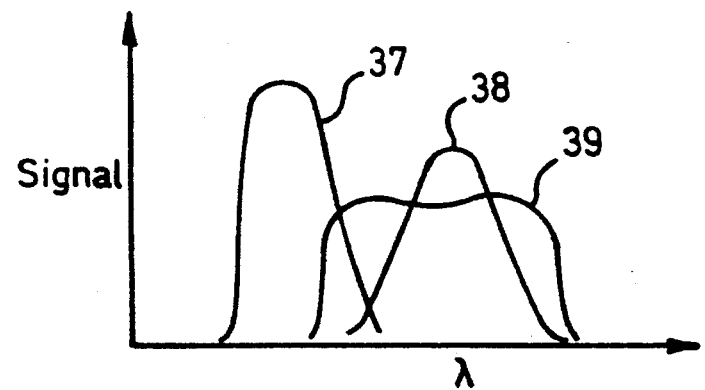

In the case of FIG. 8d, the diamond infra-red Raman signal produced is low, or zero, as the infra-red scattering characteristics 39 of mineral matter do not overlap very much with the band pass characteristics of the filter 23. However, the infra-red Raman side band signal will be very large due to the large degree of overlap of the mineral infra-red Raman signal and the band pass characteristics of the filter 22. When the latter signal is subtracted from the former, a large negative or zero value will result. Accordingly, mineral can be distinguished from diamond.

The wavelength of irradiating radiation used is in the 1 μm region, corresponding to infra-red radiation, as produced by a Nd YAG laser. When diamonds of all classes are irradiated with 1.064 μm infra-red radiation, there is scattering of the incident radiation at a Raman Anti-Stokes wavelength of 0.932 μm and a Raman Stokes wavelength of 1.2398 μm. Observation of this Raman scattered wavelength will indicate whether the object present is a diamond or not. Infra-red radiation is used in preference to other wavelengths, for example ultra-violet/visible radiation which causes luminescence in diamond and some host minerals, which may interfere with the detection of UV/visible Raman scattering spectrum of diamond. The background host minerals with which the diamonds are associated do not generally luminesce at infrared wavelengths and so are less likely to interfere with the infra-red Raman shifted characteristic scattering spectrum associated with diamond.

In the apparatus of FIGS. 4 and 5, light of the first beam is passed through a filter 23 passing substantially only infra-red Raman scattered radiation of wavelength 1.239 μm, which is focussed onto an InGaAs detector 21 by a system of lenses 25 to produce a signal responsive to the intensity of infra-red Raman radiation emitted by the object. The other beam passes through a filter 22 passing substantially only radiation to one side of the Raman filter band pass (Raman side band) to the detector 18 via lens assembly 24 to produce a second signal responsive to the intensity of background infra-red radiation at a wavelenth close to the Raman scattering wavelength, to compare the first signal with. The second signal may be substracted from the first signal.

If the Raman Anti-Stokes wavelength of 0.932 μm is to be detected, a silicon detector or photomultiplier tube (PMT) could be used.

The front cylindrical lens 14 may be for instance two Spindler and Hoyer 100 mm focal length lenses, and the cylindrical back lens 15 may be a Spindler and Hoyer 200 mm focal length lens. Preferably the lens assemblies 24 and 25 of the detectors 18 and 21 respectively comprise spherical Spindler and Hoyer 100 mm focal length lenses combined with an aspheric Spindler and Hoyer 18 mm focal length lens. Suitable Raman filters are CWL 1239.8 nm FWHM 1 nm or 2 nm made by Omega Optical Inc of America and for the Raman side band, a filter produced by Omega Optical Inc of CWL 1260 nm and 10 nm FWHM may be used. The YAG laser radiation blocking filter may be a 20 mm silicon disc produced by Span Optics Limited. The laser itself may be a Model 301 Spectron 1064 nm Nd YAG laser produced by Spectron Lasers Ltd and the detectors may be 3 μm diameter TE cooled detectors produced by ITL Limited.

Figure 9:
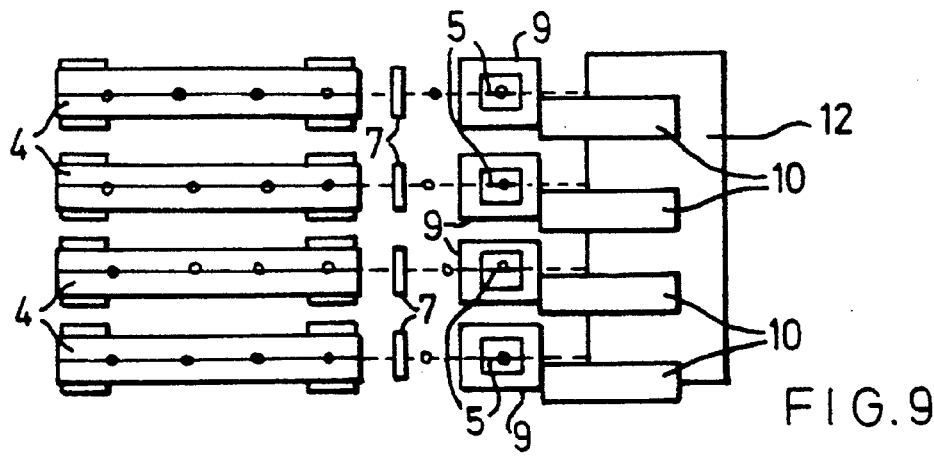
FIG. 9 is a schematic plan view of a second embodiment of a machine for classifying objects according to the invention.
Figure 10:
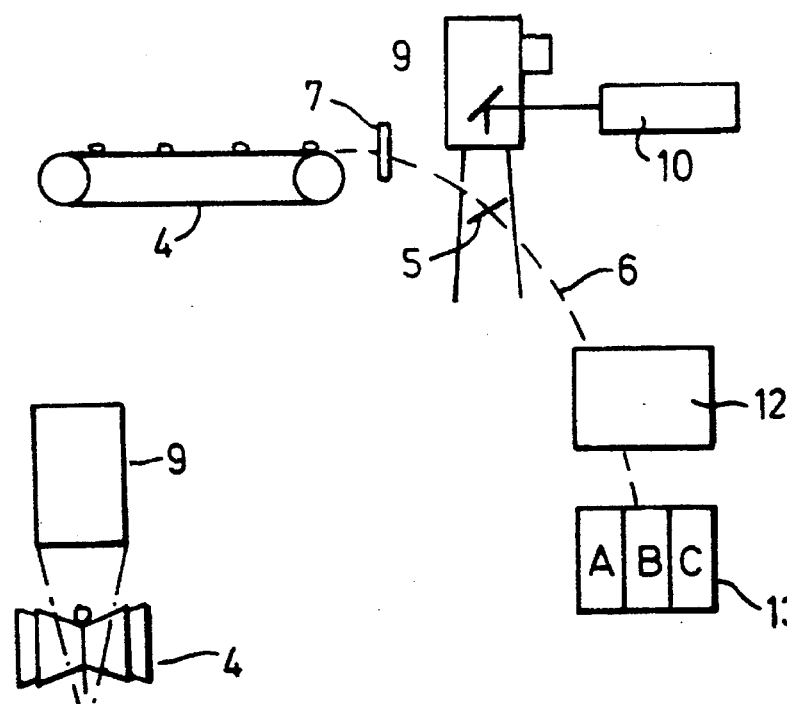
FIG. 10 is a schematic elevation of the machine of FIG. 9.
Figure 11:
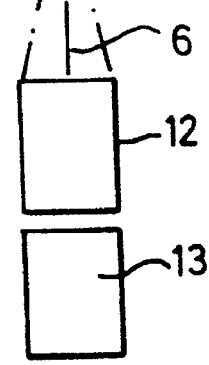
FIG. 11 is a schematic end view of the machine of FIGS. 9 and 10, looking towards the belt.

FIGS. 9 to 11 show an alternative embodiment of the apparatus of the invention. The same reference numerals are used in FIGS. 9 to 11 as are used in FIGS. 1 to 3 to indicate similar apparatus.

FIG. 9 shows a plan view of the second embodiment of the invention. Instead of a single belt, a plurality of belts 4 are used which are placed side by side. Objects are fed singly along each belt through a light curtain 7 into a viewing zone 5 where they are irradiated, the objects being sorted by dispenser 12 into bins 13. The difference between the apparatus of FIGS. 9 to 11 and FIGS. 1 to 3 lies in the arrangement of the irradiating system 9 and laser 10, which are placed above the apparatus in FIGS. 9 to 11, rather than beside it, as in FIGS. 1 to 3. As in FIGS. 1 to 3, the irradiation zone 5 comprises a rectangular irradiation zone at a substantial angle to the trajectory 6 lying in the same plane as the trajectory 6 (which trajectory is not itself substantially vertical) and is of a generally rectangular shape, being much longer than it is wide. This arrangement allows a plurality of belts to be placed side by side very close together, thus allowing a compact high volume sorter. Running a plurality of belts in parallel allows a relatively large volume of material to be processed by the apparatus. As shown in FIG. 11, radiation is focussed by irradiating means 9 onto the irradiation zone 5. Although the objects are irradiated before they reach irradiating zone 5, as they are falling through radiation from irradiating means 9, the intensity of radiation is not sufficient to cause substantial emission except in the focus at the irradiation zone 5. As shown in FIG. 10, the irradiation zone is approximately horizontal in the second embodiment and (FIG. 2) approximately vertical in the first embodiment.

The present invention has been described above purely by way of example and modifications can be made within the invention.

We claim:

1. A method of detecting diamonds in a plurality of objects, comprising:

irradiating the objects with infra-red radiation;

passing radiation emitted by the objects through a narrow band pass filter which passes radiation of a frequency different from that of the infra-red irradiating radiation by an amount corresponding to a Raman shift for diamond;

sensing the intensity of radiation having such a Raman shift passing through the filter, the sensed intensity of radiation having such a Raman shift being corrected using a signal dependent upon the size of the respective object; and identifying objects which emit radiation having such a Raman shift; wherein the objects are sorted between different corrected Raman signal levels.

2. The method of claim 1, wherein background radiation is subtracted.

3. The method of claim 1, wherein the objects are pre-sorted into size fractions.

4. The method of claim 1, wherein any said objects which emit radiation having such a Raman shift over a threshold value are identified.

5. The method of claim 1, wherein the objects are moving substantially in a single vertical plane when irradiated, and the irradiation is brought to a line focus at a substantial angle to the trajectory of the objects in said vertical plane.

6. The method of claim 1, wherein the diamonds are detected in gangue.

7. The method of claim 1 wherein the diamonds are sorted according to quality.

8. The method of claim 7, wherein the sensed intensity of radiation having such a Raman shift is corrected in relation to a signal dependent upon the size of the object, objects having a high signal being classified as high quality diamonds and objects have a low signal being classified as poor quality diamonds.

9. Apparatus for detecting diamonds in a plurality of objects, comprising:

means for irradiating the objects with infra-red radiation;

means for passing radiation emitted by the objects through a first narrow band pass filter which passes radiation having a frequency different from that of the infra-red irradiating radiation by an amount corresponding to a Raman shift for diamond;

means for providing a signal dependent upon the intensity of radiation passing through the first filter;

means for correcting the intensity signal using a signal dependent upon the size of the respective object; and means for identifying objects which emit radiation passing through the first filter, wherein the objects are sorted between different corrected Raman signal levels.

10. The apparatus of claim 9, further comprising size detection means for giving a signal dependent upon the size of the respective object.

11. The apparatus of claim 9, further comprising a second narrow band pass filter which passes radiation of a frequency different to that passed by the first narrow band pass filter;

means for providing a second signal dependent upon the intensity of radiation passing through the second filter; and means for correcting the signal dependent upon the intensity of radiation passing through the first filter using the second signal.

12. A method according to claim 1, of processing diamondiferous ore in which ore is passed through at least one object size reduction means, the method comprising detecting diamonds in the ore before the ore is fed into said at least one object size reduction means, wherein the detecting step comprises irradiating the objects with infra-red radiation, passing radiation emitted by the objects through a narrow band pass filter which passes radiation of a frequency different from that of the infra-red irradiating radiation by an amount corresponding to a Raman shift of diamond, sensing the intensity of radiation passing through the filter, and identifying objects which emit radiation having such a shift.

13. The apparatus according to claim 9 for processing diamondiferous ore, comprising:

means for detecting diamonds in the ore; and at least one object size reduction means for receiving objects from the detecting means;

wherein the detecting means comprises:

means for irradiating the objects with infra-red radiation;

means for passing radiation emitted by the objects through a narrow band pass filter which passes radiation having a frequency different from that of the infra-red irradiating radiation by an amount corresponding to a Raman shift for diamond;

means for sensing radiation passing through the filter; and means for identifying objects which emit radiation passing through the filter.

* * * * *